United States Patent
Suzuki et al.

(10) Patent No.: US 7,912,251 B2
(45) Date of Patent: Mar. 22, 2011

(54) EYELID DETECTION APPARATUS AND PROGRAM THEREFOR

(75) Inventors: Tomoharu Suzuki, Anjo (JP); Jun Adachi, Obu (JP); Shinichi Kojima, Nisshin (JP); Kenichi Ohue, Toyota (JP); Yuji Ninagawa, Nishikamo-gun (JP)

(73) Assignees: Aisin Seiki Kabushiki Kaisha, Aichi-ken (JP); Toyota Jidosha Kabushiki Kaisha, Aichi-ken (JP)

( * ) Notice: Subject to any disclaimer, the term of this patent is extended or adjusted under 35 U.S.C. 154(b) by 592 days.

(21) Appl. No.: 12/046,715

(22) Filed: Mar. 12, 2008

(65) Prior Publication Data

US 2008/0226138 A1 Sep. 18, 2008

(30) Foreign Application Priority Data

Mar. 14, 2007 (JP) ................................. 2007-065529

(51) Int. Cl.
  *G06K 9/00* (2006.01)
  *H04N 9/47* (2006.01)
  *G03B 17/00* (2006.01)

(52) U.S. Cl. .............................. 382/117; 348/78; 396/51

(58) Field of Classification Search .................. 382/117, 382/168, 173, 195, 199, 266, 283, 312; 351/200; 600/558–559; 348/78; 396/18, 51
See application file for complete search history.

(56) References Cited

U.S. PATENT DOCUMENTS

| | | | | |
|---|---|---|---|---|
| 4,862,410 A | * | 8/1989 | Fukunaga | 715/201 |
| 5,432,866 A | * | 7/1995 | Sakamoto | 382/128 |
| 5,657,110 A | * | 8/1997 | Konishi | 351/212 |
| 5,751,836 A | | 5/1998 | Wildes et al. | |
| 6,419,638 B1 | * | 7/2002 | Hay et al. | 600/558 |
| 6,542,624 B1 | * | 4/2003 | Oda | 382/117 |
| 7,130,453 B2 | * | 10/2006 | Kondo et al. | 382/117 |
| 7,593,550 B2 | * | 9/2009 | Hamza | 382/117 |
| 2003/0169907 A1 | | 9/2003 | Edwards et al. | |

FOREIGN PATENT DOCUMENTS

| | | |
|---|---|---|
| JP | 7-313459 A | 12/1995 |
| JP | 3143819 B2 | 1/2001 |
| JP | 2004-220080 A | 8/2004 |
| WO | 02/09025 A1 | 1/2002 |

OTHER PUBLICATIONS

Extended European Search Report dated Mar. 10, 2010 (6 pages).

* cited by examiner

*Primary Examiner* — Kanji Patel
(74) *Attorney, Agent, or Firm* — Sughrue Mion, PLLC

(57) ABSTRACT

An eyelid detection apparatus includes edge image generating means for generating an edge image representing a magnitude of pixel value change per pixel in a predetermined direction in a region including an eye, based upon an image of the region; local peak value point searching means for searching a local peak value point, where the magnitude of pixel value change reaches a local peak value in the predetermined direction, in the edge image; and boundary point detecting means for detecting at least one of a first boundary point indicating a boundary between an upper eyelid and an eyeball and a second boundary point indicating a boundary between a lower eyelid and the eyeball, based upon a point which is shifted from the local peak value point in a direction towards the eyeball.

15 Claims, 12 Drawing Sheets

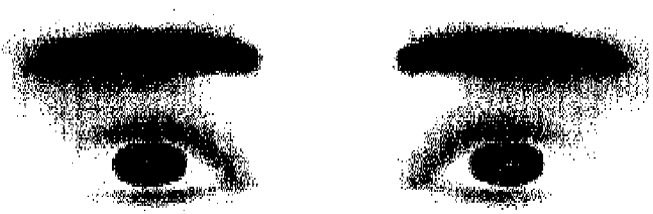
FIG. 2A
FIG. 2B
FIG. 3
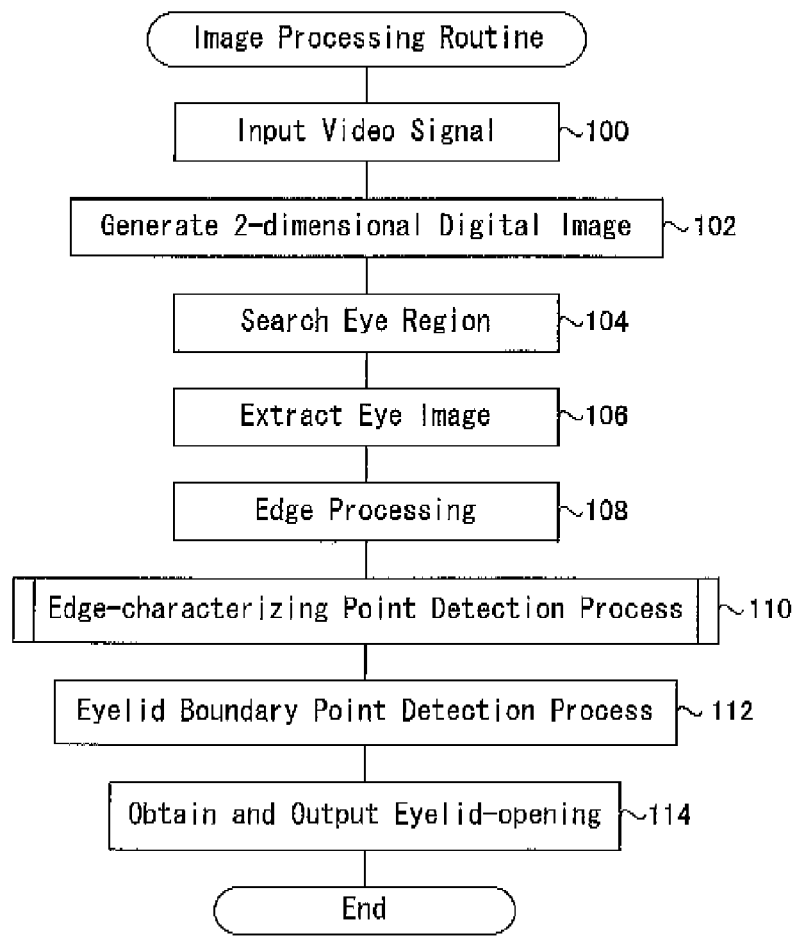

FIG.4A Sobel Filter

| 1 | 2 | 1 |
|---|---|---|
| 0 | 0 | 0 |
| -1 | -2 | -1 |

FIG.4B Prewitt Filter

| 1 | 1 | 1 |
|---|---|---|
| 0 | 0 | 0 |
| -1 | -1 | -1 |

FIG.4C Simple Difference Filter

| 1 | 0 | -1 |
|---|---|---|

FIG.4D Simple Difference Filter for Smoothing

| 1 | 2 | 0 | -2 | -1 |
|---|---|---|---|---|

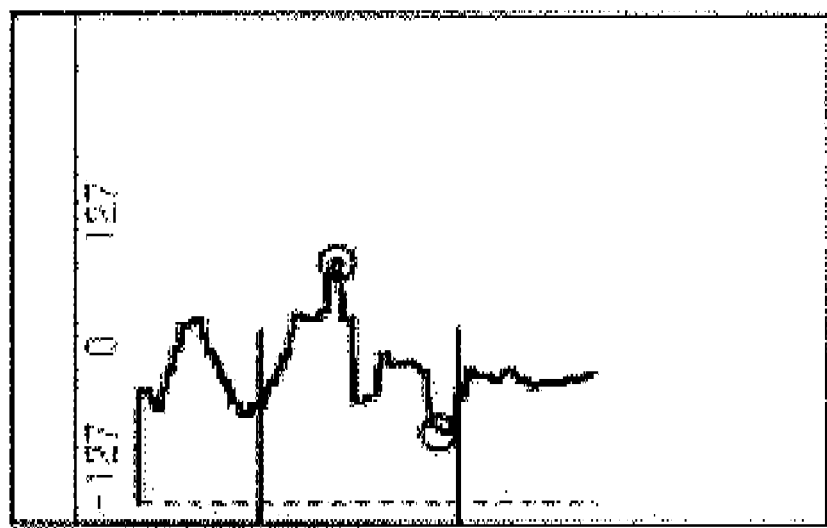
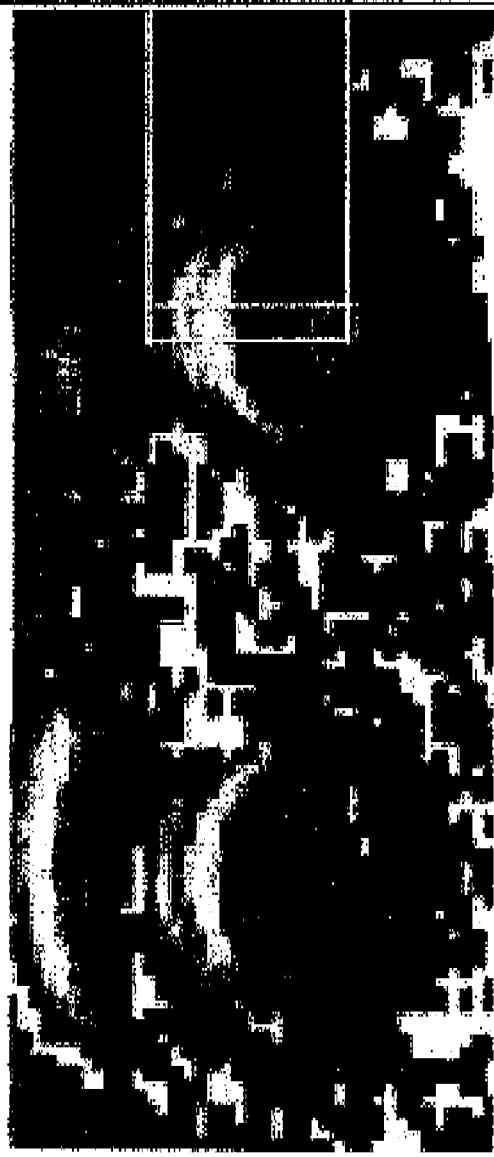

Edge-Calculation Threshold D1

Edge-Calculation Threshold D1

Edge-Calculation Threshold D1

D2  -0  D1

EYELID DETECTION APPARATUS AND PROGRAM THEREFOR

CROSS REFERENCE TO RELATED APPLICATIONS

This application is based on and claims priority under 35 U.S.C. §119 to Japanese Patent Application 2007-065529, filed on Mar. 14, 2007, the entire content of which is incorporated herein by reference.

FIELD OF THE INVENTION

This invention generally relates to an eyelid detection apparatus and a program therefor. Specifically, this invention pertains to an eyelid detection apparatus, which detects a boundary point of an eyelid from an image including a region having an eye, and a program therefor.

BACKGROUND

Eyelid opening-extent detection apparatuses have been conventionally known. Japanese Patent No. 3143819 discloses therein an eyelid opening-extent detection apparatus, which detects a boundary point of an upper eyelid and an eyeball based upon a local maximal value point which has an edge value being a local maximal value or detects a boundary point of a lower eyelid and the eyeball based upon a local minimal value point which has an edge value being a local minimal value. Each boundary point is detected in a one-dimensional edge image representing a magnitude of grayscale change in a grayscale image. Specifically, the eyelid opening-extent detection apparatus searches edge local peak value points located most outward and determines the edge local peak value points searched as the boundary point of the upper eyelid and the eyeball and the boundary point of the lower eyelid and the eyeball, respectively.

However, the above described apparatus determines the edge local peak value points on the one-dimensional edge image, each of which has an edge value reaching maximum (upper eyelid) or minimum (lower eyelid), as the boundary points. In a case where an eyelid of an individual such as a driver is colored, such as where the eyelid is applied with eye shadow, a point distant from a boundary between the eyelid and an eyeball is erroneously detected as a boundary point. This may cause an erroneous detection of a boundary point.

A need thus exists for an eyelid detection apparatus and a program therefor, which are not susceptible to the drawback mentioned above.

SUMMARY OF THE INVENTION

According to an aspect of the present invention an eyelid detection apparatus includes edge image generating means for generating an edge image representing a magnitude of pixel value change per pixel in a predetermined direction in a region including an eye, based upon an image of the region, local peak value point searching means for searching a local peak value point, where the magnitude of pixel value change reaches a local peak value in the predetermined direction, in the edge image generated by the edge image generating means; and boundary point detecting means for detecting at least one of a first boundary point indicating a boundary between an upper eyelid and an eyeball and a second boundary point indicating a boundary between a lower eyelid and the eyeball, based upon a point which is shifted from the local peak value point searched by the local peak value point searching means in a direction towards the eyeball.

A program instructs a computer to execute processes of: generating an edge image representing a magnitude of pixel value change per pixel in a predetermined direction in a region including an eye, based upon an image of the region; searching a local peak value point, where the magnitude of pixel value change reaches a local peak value in the predetermined direction, in the edge image; and detecting at least one of a first boundary point indicating a boundary between an upper eyelid and an eyeball and a second boundary point indicating a boundary between a lower eyelid and the eyeball, based upon a point which is shifted from the local peak value point in a direction towards the eyeball.

BRIEF DESCRIPTION OF THE DRAWINGS

The foregoing and additional features and characteristics of the present invention will become more apparent from the following detailed description considered with reference to the accompanying drawings, wherein:

FIG. 2A is a diagram illustrating an eye image of an individual being used as subject;

FIG. 2B is a diagram illustrating a Sobel edge image of the eye image in FIG. 2A;

FIG. 3 is a flowchart for explaining an image processing routine implemented by the eyelid detection apparatus according to the first embodiment;

FIG. 4A is a diagram illustrating a Sobel filter;

FIG. 4B is a diagram illustrating a Prewitt filter;

FIG. 4C is a diagram illustrating a Simple Difference Filter;

FIG. 4D is a diagram illustrating a Simple Difference Filter for Smoothing;

FIG. 5A is a diagram illustrating a Sobel edge image;

FIG. 5B is a graph summarizing changes in edge values in the Sobel edge image in FIG. 5A;

DETAILED DESCRIPTION

Embodiments of the present invention will be described below with reference to the attached drawing figures. The present invention for example applies to an eyelid detection apparatus obtaining an eyelid-opening from a grayscale image and outputting the eyelid-opening.

Figure 1:
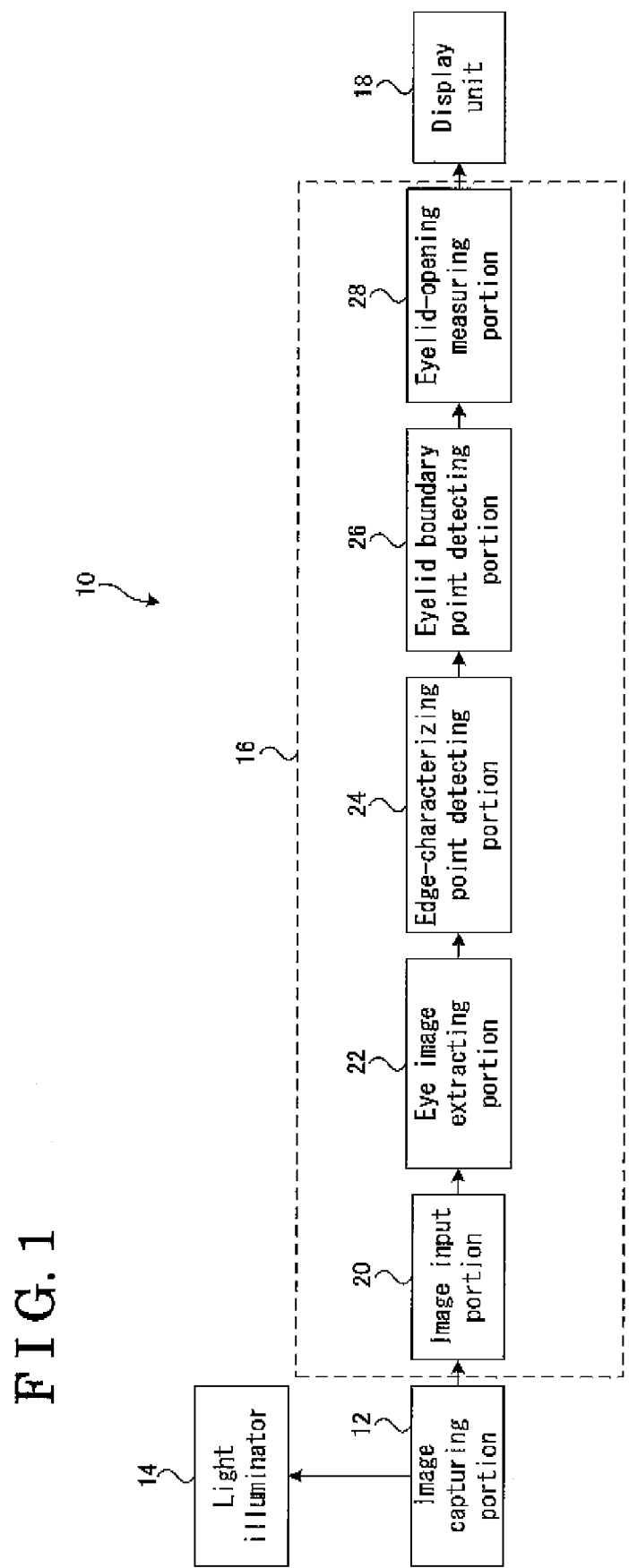
FIG. 1 is a schematic block diagram illustrating an eyelid detection apparatus according to a first embodiment of the present invention.

As illustrated in FIG. 1, an eyelid detection apparatus 10 of a first embodiment of the present invention includes an image capturing portion 12, a light illuminator 14, a computer 16 and a display unit 18. The image capturing portion 12 is configured with, for example a CCD (charge coupled device) camera for capturing an image containing a face of an individual being used as a subject (herein referred to as the subject) such as a driver or other passengers. The light illuminator 14 is configured with, for example an infrared strobe, an infrared LED (light emitting diode), or the like and operates in synchronization with an operation of a shutter of the image capturing portion 12 and supplies any necessary light illumination to enable the image capturing portion 12 to capture the subject. The computer 16 implements an image processing. The display unit 18 is configured with, for example a CRT (cathode ray tube).

The computer 16 contains therein a CPU, a ROM (read only memory) memorizing programs for executing an image processing routine described later, a RAM (random access memory) memorizing data and so on, and a bus connecting these elements. The computer 16 is now described below by being divided into means (portions) for implementing functions determined based upon hardware and software. As illustrated in FIG. 1, the computer 16 includes an image input portion 20, an eye image extracting portion 22, an edge-characterizing point detecting portion 24, an eyelid boundary point detecting portion 26, and an eyelid-opening measuring portion 28. The image input portion 20 is inputted with a facial image being a grayscale image (e.g., a black and white image") outputted by the image capturing portion 12. The eye image extracting portion 22 extracts an image of a small segment having one or both eyes from the facial image outputted by the image input portion 20. The image of the small segment having one or both eyes is hereinafter referred to as an eye image. The edge-characterizing point detecting portion 24 performs an eye image processing based upon the eye image extracted by the eye image extracting portion 22 and detects and plots edge-characterizing point. The eyelid boundary point detecting portion 26 detects a boundary point of an eyelid and an eyeball based upon the edge-characterizing points detected by the edge-characterizing point detecting portion 24. An eyeball herein includes a round portion, which is usually colored black or blue, a white portion at the left side of the round portion, and a white portion at the right side of the round portion. The eyelid-opening measuring portion 28 measures an eyelid-opening based upon the boundary points detected by the eyelid boundary point detecting portion 26. The eyelid-opening includes an opening extent of an eyelid.

The image input portion 20 is configured with, for example an A/D convertor, an image memory storing image data being a single screen, and so on.

The eye image extracting portion 22 searches a region including one or both eyes (hereinafter referred to as an eye region) from the facial image to identify a position where the small segment should be extracted. The eye image extracting portion 22 then extracts an image of the small segment having one or both eyes with reference to the identified position. The image of the small segment is employed as an eye image.

The edge-characterizing point detecting portion 24 generates a Sobel edge image illustrated in FIG. 2B from an eye image illustrated in FIG. 2A with a Sobel operator. The Sobel edge image illustrated in FIG. 2B shows a magnitude of grayscale change per pixel in a direction heading from an upper portion of the eye region to a lower portion thereof, i.e., in a blinking direction. The magnitude of grayscale change can be represented by a magnitude of pixel value change per pixel in a predetermined direction, e.g., in the blinking direction. The magnitude of grayscale change or pixel value change corresponds to an edge value. The edge-characterizing point detecting portion 24 searches points where an edge value reaches a local maximal value or a local minimal value in the Sobel edge image generated and detects edge-characterizing points based upon the points. Such point corresponds to a local peak value point, a local maximal value point and/or a local minimal value point. The local maximal value and the local minimal value each correspond to a local peak value.

The eyelid boundary point detecting portion 26 detects a first boundary point reflecting a boundary between an upper eyelid and an eyeball based upon the edge-characterizing point at the upper eyelid. The eyelid boundary point detecting portion 26 further detects a second boundary point reflecting a boundary between a lower eyelid and the eyeball based upon the edge-characterizing point at the lower eyelid.

The eyelid-opening measuring portion 28 measures a distance between the first boundary point and the second boundary point and outputs the distance as an eyelid-opening (an opening extent of the eyelid).

Described below is an operation of the eyelid detection apparatus 10. First of all, the image capturing portion 12 captures a facial image of individual being used as the subject. At this point, in order to reduce influences of disturbance light occurring in an ambient, for example the light illuminator 14 structured with an infrared strobe can be employed to be synchronized with the facial image capturing of the image capturing portion 12 and illuminate a facial portion of the individual being used as the subject. Moreover, when the light illuminator 14 can provide continuous light, the light illuminator 14 does not have to be synchronized with the operation of the image capturing portion 12, thereby simplifying the structure of the light illuminator 14.

The computer 16 then implements an image processing routine illustrated in FIG. 3. In Step 100, the computer 16 controls the image input portion 20 to be inputted with a facial image captured by the image capturing portion 12 as a video signal. In Step 102, the video signal is A/D converted so as to generate a two-dimensional digital image. According to the first embodiment, the following steps are executed with digital processing using the two-dimensional digital image, so that the word "image" hereinafter represents the digital image.

In Step 104, the computer 16 controls the eye image extracting portion 22 to search an eye region in the facial image and to determine a region having one or both eyes as an extracted region. In Step 106, the eye image extracting portion 22 extracts a small segment including one eye as an eye image. The eye region can be searched with methods, such as image processing with template matching. The eye region alternatively can be searched by an operator's manual operation with an eye region indicating means, such as a keyboard, a mouse device, an electronic pen or a light pen.

In Step 108, the computer 16 controls the edge-characterizing point detecting portion 24 to apply edge processing using a Sobel filter illustrated in FIG. 4A to the eye image extracted in Step 106. The edge-characterizing point detecting portion 24 then generates a Sobel edge image being a one-dimensional edge image representing a magnitude of grayscale change. The magnitude of grayscale change corresponds to a magnitude of pixel value change per pixel in a predetermined direction, i.e., in a direction heading from an upper portion of the eye region to a lower portion thereof. According to one example, where (x, y) represents values of coordinates of a point of a current image and A(x, y) represents a pixel value of a current point, an edge value E(x, y) of the point in the Sobel edge image is expressed as follows:

$$E(x,y)=A(x-1,y-1)+2A(x,y-1)+A(x+1,y-1)-A(x-1,y+1)-2A(x,y+1)-A(x+1,y+1).$$

According to the first embodiment, a Sobel filter is employed for the purpose of edge processing. Alternatively, a Prewitt filter in FIG. 4B, a Simple Difference Filter in FIG. 4C, and a Simple Difference Filter for Smoothing in FIG. 4D, or the like may be employed.

Through the edge processing in Step 108, variations in the magnitude of pixel value change in a blinking direction of an initial image, i.e., in a direction heading from an upper portion of an initial image to a lower portion thereof, are obtained as illustrated in FIG. 5B. In general, an eyeball exhibits less reflectance than an eyelid being human skin, thereby causing darkening of the eyeball when captured as an image. Therefore, with respect to a direction heading from an upper portion of an initial image to a lower portion thereof, pixel intensity values at the upper eyelid region change from "bright" to "dark" in a downward direction in FIG. 5A, while pixel intensity values at the lower eyelid region change from "dark" to "bright" in the downward direction in FIG. 5A. As a result, an edge value obtained at a boundary between an upper eyelid and an eyeball is recognized as a local maximal value, while an edge value obtained at a boundary between a lower eyelid and the eyeball is recognized as a local minimal value. Further, the eyeball is located at a lower side of a point having the local maximal value and at an upper side of a point having the local minimal value.

Figure 6:
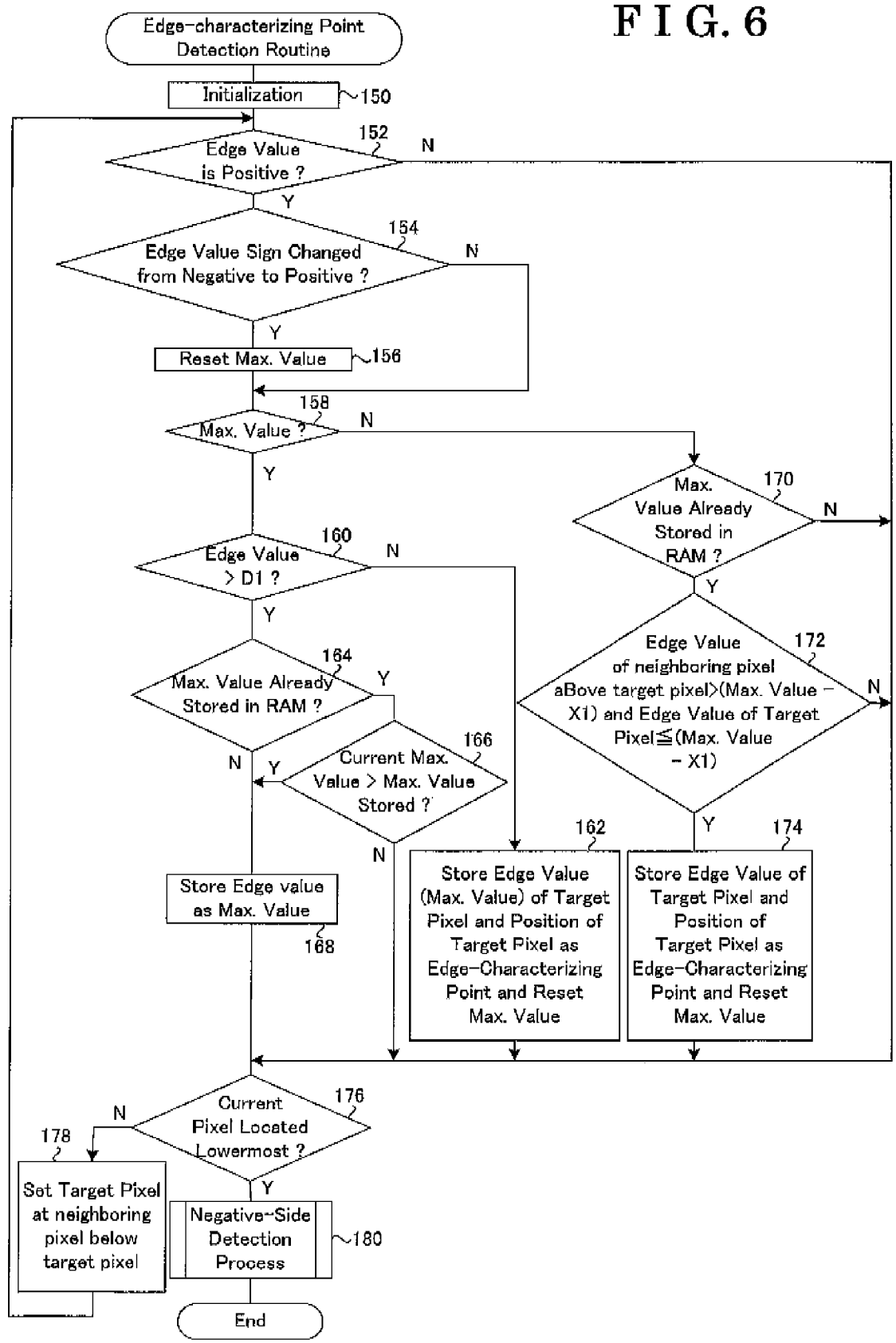
FIG. 6 is a flowchart for explaining an edge-characterizing point detection routine implemented by the eyelid detection apparatus according to the first embodiment.

In Step 110 the computer 16 controls the edge-characterizing point detecting portion 24 to implement a processing for detecting an edge-characterizing point. An edge-characterizing point detection routine to execute Step 110 will be described below with reference to FIG. 6. The edge-characterizing point detection routine is implemented respectively for multiple pixel rows, each pixel row consisting of multiple picture elements arranged in a vertical direction of the eye image, i.e., in the up-and-down direction in FIG. 5.

In Step 150, the computer 16 controls the RAM to clear a local maximal value stored therein and initializes to set a target picture element (hereinafter referred to as a target pixel) at an initial position that is located uppermost on a baseline of the current pixel row. In Step 152, the computer 16 judges whether an edge value of the target pixel is positive. When an affirmative answer "Yes" is obtained in Step 150, i.e., when the edge value of the target pixel is positive, the routine program proceeds to Step 154. In Step 154, the computer 16 judges whether a sign of the edge value has changed from negative to positive between a neighboring pixel above the target pixel and the target pixel. The neighboring pixel above the target pixel is a neighboring pixel which is one pixel above the target pixel. When a negative answer "No" is obtained in Step 154, i.e., when the sign of the edge value has not changed from negative to positive, the program proceeds to Step 158. On the other hand, when an affirmative answer "Yes" is obtained in Step 154, i.e., when the sign of the edge value has changed from negative to positive, the program proceeds to Step 156. In Step 156, the computer 16 controls the RAM to clear the local maximal value already stored therein, and the program proceeds to Step 158.

In Step 158, the computer 16 judges whether the edge value of the target pixel is possibly a local maximal value in an up-down direction on the baseline. Here, the judgment in Step 158 is implemented based upon edge values, of the neighboring pixel above the target pixel, the target pixel and a neighboring pixel below the target pixel. The neighboring pixel below the target pixel is a neighboring pixel which is one pixel below the target pixel. When the edge value of the target pixel is determined to be a local maximal value, the program proceeds to Step 160. In Step 160, the computer 16 judges whether the local maximal value being the edge value of the target pixel is greater than a predetermined first threshold value D1. When a negative answer "No" is obtained in Step 160, i.e., when the local maximal value being the edge value of the target pixel is less than, or equal to, the first threshold value D1, the program proceeds to Step 162. In Step 162, the computer 16 stores a position of the target pixel as an edge-characterizing point and controls the RAM to clear the local maximal value stored therein. The program then proceeds to Step 176. In Step 162, the computer 16 controls the RAM to also store the edge value at the edge-characterizing point.

On the other hand, when an affirmative answer "Yes" is obtained in Step 160, i.e., when the local maximal value being the edge value of the target pixel is greater than the first threshold value D1, the program proceeds to Step 164. In Step 164, the computer 16 judges a presence, or an absence, of a local maximal value already stored in the RAM. When an affirmative answer "Yes" is obtained in Step 164, i.e., when the computer 16 determines the presence of the local maximal value already stored in the RAM, the program proceeds to Step 166. In Step 166, the computer 16 judges whether the local maximal value of the target pixel at this cycle is greater than the local maximal value already stored in the RAM. When a negative answer "No" is obtained in Step 166, i.e., when the local maximal value of the target pixel at this cycle is less than, or equal to, the local maximal value already stored, the program proceeds to Step 176. Meanwhile, when an affirmative answer "Yes" is obtained in Step 166, i.e., when the local maximal value of the target pixel at this cycle is greater than the local maximal value already stored, the program proceeds to Step 168. In Step 168, the computer 16 controls the RAM to memorize the local maximal value of the target pixel at this cycle. The program then proceeds to Step 176.

In a case where there is no detection of a presence of a local maximal value already stored in the RAM in Step 164 after a local maximal value is cleared in Step 156, the program proceeds to Step 168. In Step 168, the computer 16 controls the RAM to store the local maximal value of the target pixel at this cycle.

In a case where the computer 16 determines in Step 158 that the edge value of the target pixel is not a local maximal value, a negative answer "No" is obtained in Step 158 and the program proceeds to Step 170. In Step 170, the computer 16 judges a presence, or an absence, of a local maximal value already stored in the RAM. When an affirmative answer "Yes" is obtained in Step 170, i.e., when the computer 16 detects a presence of a local maximal value already stored in the RAM, the program proceeds to Step 172. In Step 172, the computer 16 judges two conditions, whether the edge value of the neighboring pixel above the target pixel is greater than (local maximal value stored in the RAM−set value X1) and whether the edge value of the target pixel is less than, or equal to, (local maximal value stored in the RAM−set value X1). The set value X1 is defined by experimentally or statistically obtaining an edge value at a boundary point of an upper eyelid in the event that the upper eyelid is applied with eye shadow and by obtaining a difference between a local maximal value and the edge value at the boundary point of the upper eyelid. That is, the difference is pre-set as the set value X1.

Figure 7:
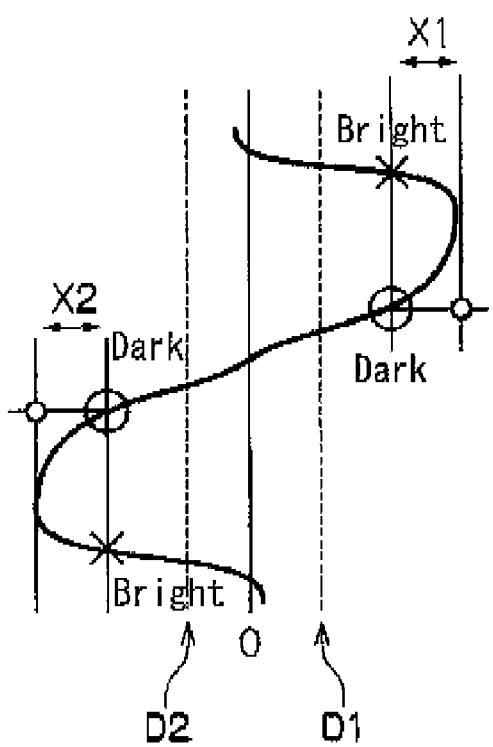
FIG. 7 is a diagram for explaining edge-characterizing points detected through the edge-characterizing point detection routine in FIG. 6.

When the computer 16 determines in Step 172 that the edge value of the neighboring pixel above the target pixel is smaller than, or equal to, (local maximal value stored in the RAM−set value X1) or that the edge value of the target pixel is greater than (local maximal value stored in the RAM−set value X1), the program proceeds to Step 176. On the other hand, when the computer 16 determines in Step 172 that the edge value of the neighboring pixel above the target pixel is greater than (local maximal value stored in the RAM−set value X1) and that the edge value of the target pixel is smaller than, or equal to, (local maximal value stored in the RAM−set value X1), the computer 16 determines that the target pixel is a point, which is closer to the dark side (area) in the variation (bright to dark) of pixel intensity value in the up-down direction, has an edge value being smaller by the set value X1 than the local maximal value, and is positioned closest to a local maximal value point from among points respectively having edge values being smaller by the set value X1 than the local maximal value, as illustrated in FIG. 7. The program then proceeds from Step 172 to Step 174. In Step 174, the computer 16 stores the position of the target pixel as an edge-characterizing point and clears the local maximal value already stored in the RAM. The program proceeds to Step 176. In Step 174, the computer 16 also stores an edge value at the edge-characterizing point in the RAM. As a result as illustrated in FIG. 7, it is possible to detect a point, which is shifted from the local maximal value point (corresponding to the local peak value point) in an up-down direction heading towards the eyeball, has an edge value being smaller by the set value X1 (corresponding to a predetermined value) tan the local maximal value, and is positioned closest to the local maximal value point, as an edge-characterizing point.

In the event where the computer 16 detects in Step 170 an absence of a local maximal value already stored in the RAM after a local maximal value is cleared in Step 156, the program proceeds directly to Step 176.

When the computer 16 determines in Step 152 that an edge value is negative, the program proceeds directly to Step 176.

In Step 176, the computer 16 judges whether the target pixel is located lowermost on the baseline of the pixel row. When the target pixel is located lowermost on the baseline of the pixel row and the above-described processes are applied to all picture elements on the baseline of the pixel row, an affirmative answer "Yes" is obtained in Step 176. The program then proceeds to Step 180. On the other hand, when the target pixel is not located lowermost on the baseline of the pixel row, a negative answer "No" is obtained in Step 176. The program in this case proceeds to Step 178. In Step 178, the computer 16 sets a neighboring pixel below the target pixel as a new target pixel. The program then returns to Step 152 so as to perform the above-described processes against the new target pixel.

Figure 8:
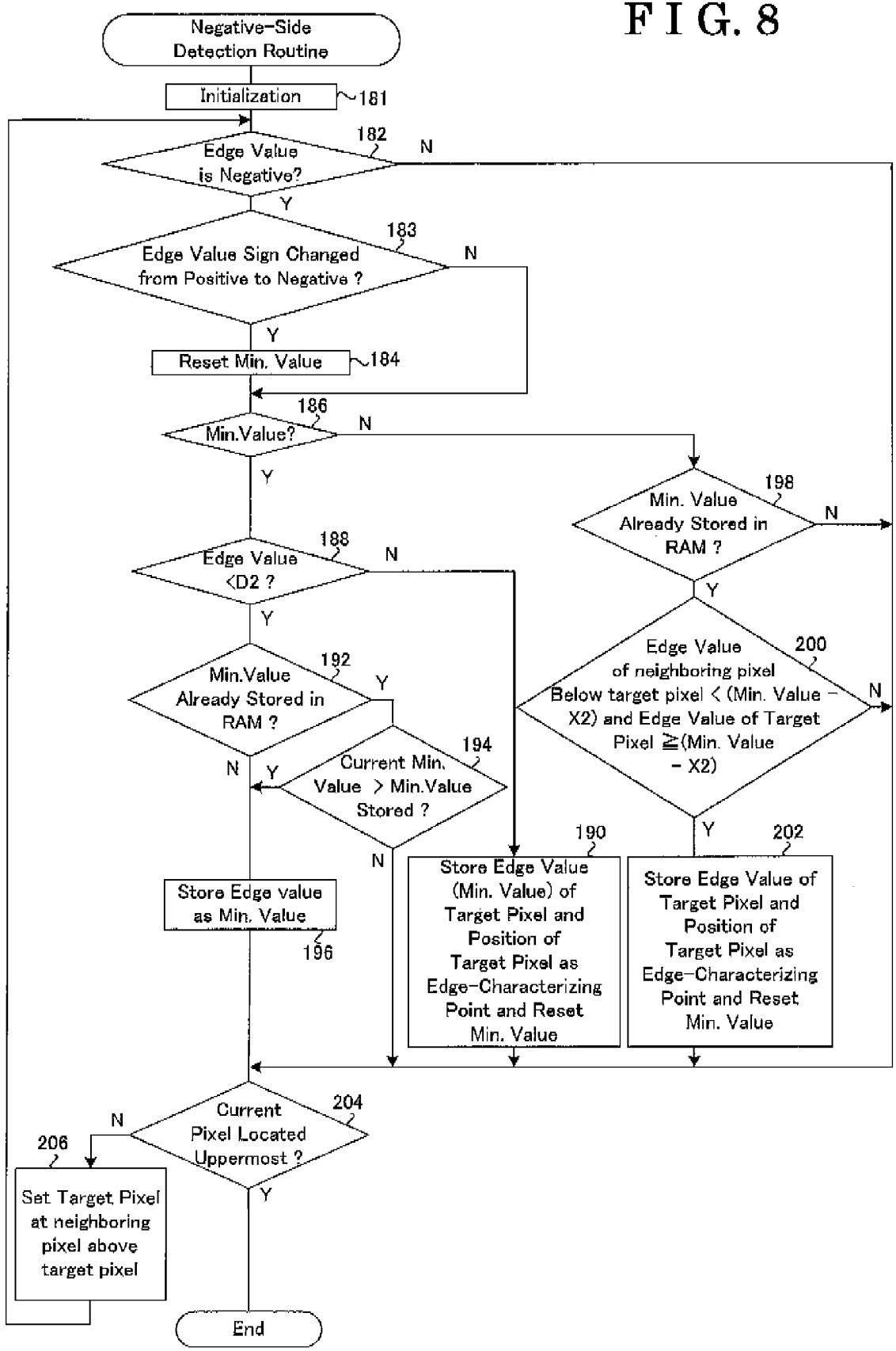
FIG. 8 is a flowchart for explaining a negative-side detection processing routine implemented by the eyelid detection apparatus according to the first embodiment.

In Step 180, the computer 16 implements negative-side detection processing and temporarily terminates the edge-characterizing point detection routine. Here, a negative-side detection processing routine to achieve Step 180 is described below with reference to FIG. 8.

In Step 181, the computer 16 controls the RAM to clear a local minimal value stored therein and initializes to set a target picture element (hereinafter referred to as a target pixel) at an initial position that is located lowermost on a baseline of the current pixel row. In Step 182, the computer 16 judges whether an edge value of the target pixel is negative. When an affirmative answer "Yes" is obtained in Step 182, i.e., when the edge value of the target pixel is negative, the routine program proceeds to Step 183. In Step 183, the computer 16 judges whether a sign of the edge value has changed from positive to negative between a neighboring pixel below the target pixel and the target pixel. The neighboring pixel below the target pixel is a neighboring pixel which is one pixel below the target pixel. When a negative answer "No" is obtained in Step 184, i.e., when the sign of the edge value has not changed from positive to negative, the program proceeds to Step 186. On the other hand, when an affirmative answer "Yes" is obtained in Step 184, i.e., when the sign of the edge value has changed from positive to negative, the program proceeds to Step 184. In Step 184, the computer 16 controls the RAM to clear the local minimal value already stored therein, and the program proceeds to Step 186.

In Step 186, the computer 16 judges whether the edge value of the target pixel is possibly a local minimal value in an down-to-up direction on the baseline. Here, the judgment in Step 186 is implemented based upon edge values, of a neighboring pixel above the target pixel, the target pixel and the neighboring pixel below the target pixel. The neighboring pixel above the target pixel is a neighboring pixel which is one pixel above the target pixel. When the edge value of the target pixel is determined to be a local minimal value, the program proceeds to Step 188. In Step 188, the computer 16 judges whether the local minimal value being the edge value of the target pixel is smaller tan a predetermined second threshold value D2 (D2<0). When a negative answer "No" is obtained in Step 188, i.e., when the local minimal value being the edge value of the target pixel is greater than, or equal to, the second threshold value D2, the program proceeds to Step 190. In Step 190, the computer 16 stores a position of the target pixel as an edge-characterizing point and controls the RAM to clear the local minimal value stored therein. The program then proceeds to Step 204. In Step 190, the computer 16 controls the RAM to also store the edge value at the edge-characterizing point.

On the other hand, when an affirmative answer "Yes" is obtained in Step 188, i.e., when the local minimal value being the edge value of the target pixel is smaller than the second threshold value D2, the program proceeds to Step 192. In Step 192, the computer 16 judges a presence, or an absence, of a local minimal value already stored in the RAM. When an affirmative answer "Yes" is obtained in Step 192, i.e., when the computer 16 determines the presence of the local minimal value already stored in the RAM, the program proceeds to Step 194. In Step 194, the computer 16 judges whether the local minimal value of the target pixel at this cycle is smaller than the local minimal value already stored in the RAM. When a negative answer "No" is obtained in Step 194, i.e., when the local minimal value of the target pixel at his cycle is greater than, or equal to, the local minimal value already stored, the program proceeds to Step 204. Meanwhile, when an affirmative answer "Yes" is obtained in Step 194, i.e., when the local minimal value of the target pixel at this cycle is smaller than the local minimal value already stored, the program proceeds to Step 196. In Step 196, the computer 16 controls the RAM to memorize the local minimal value of the target pixel at is cycle. The program then proceeds to Step 204.

In a case where there is no detection of a presence of a local minimal value already stored in the RAM in Step 192 after a local minimal value is cleared, the program proceeds to Step 196. In Step 196, the computer 16 controls the RAM to store the local minimal value of the target pixel at this cycle.

In a case where the computer 16 determines in Step 186 that the edge value of the target pixel is not a local minimal value, a negative answer "No" is obtained in Step 186 and the program proceeds to Step 198. In Step 198, the computer 16 judges a presence, or an absence, of a local minimal value already stored in the RAM. When an affirmative answer "Yes" is obtained in Step 198, i.e., when the computer 16 detects a presence of a local minimal value already stored in the RAM, the program proceeds to Step 200. In Step 200, the computer 16 judges two conditions, whether the edge value of the neighboring pixel below the target pixel is smaller than (local minimal value stored in the RAM−set value X2) and whether the edge value of the target pixel is greater than, or equal to, (local minimal value stored in the RAM−set value X2). The set value X2 (X2<0) is defined by experimentally or statistically obtaining an edge value at a boundary point of a lower eyelid in the event that the lower eyelid is applied with eye shadow and by obtaining a difference between a local minimal value and the edge value at the boundary point of the lower eyelid. That is, the difference is pre-set as the set value X2.

When the computer 16 determines in Step 200 that the edge value of the neighboring pixel below the target pixel is greater than, or equal to, (local minimal value stored in the RAM−set value X2) or that the edge value of the target pixel is smaller than (local minimal value stored in the RAM−set value X2), the program proceeds to Step 204. On the other hand, when the computer 16 determines in Step 200 that the edge value of the neighboring pixel below the target pixel is smaller than (local minimal value stored in the RAM−set value X2) and that the edge value of the target pixel is greater than, or equal to, (local minimal value stored in the RAM−set value X2), the computer 16 determines that the target pixel is a point closer to the dark side (area) in the variation (dark to bright) of pixel intensity value in the up-down direction, has an edge value being smaller by the set value X2 (the edge value corresponding to the predetermined value) than the local minimal value, and is positioned closest to a local minimal value point (corresponding to the local peak value point) from among points respectively having edge values being smaller by the set value X2 than the local minimal value, as illustrated in FIG. 7. The program ten proceeds from Step 200 to Step 202. In Step 202, the computer 16 stores the position of the target pixel as an edge-characterizing point and clears the local minimal value already stored in the RAM. The program proceeds to Step 204. In Step 202, the computer 16 also stores an edge vale at the edge-characterizing point in the RAM. As a result, as illustrated in FIG. 7, it is possible to detect a point, which is shifted from the local minimal value point in a down-to-up direction heading towards the eyeball, has an edge value being smaller by the set value X2 than the local minimal value, and is positioned closest to the local minimal value point, as illustrated in FIG. 7.

In the event where the computer 16 detects in Step 198 an absence of a local minimal value already stored in the RAM after a local minimal value is cleared, the program proceeds directly to Step 204.

When the computer 16 determines in Step 182 that an edge value is positive, the program proceeds directly to Step 204.

In Step 204, the computer 16 judges whether the target pixel is located uppermost on the baseline of the pixel row. When the target pixel is located uppermost on the baseline of the pixel row and the below-described processes are applied to all picture elements on the baseline of the pixel row, an affirmative answer "Yes" is obtained in Step 204 and the negative-side detection routine is temporarily terminated. On the other hand, when the target pixel is not located uppermost on the baseline of the pixel row, a negative answer "No" is obtained in Step 204. The program in this case proceeds to Step 206. In Step 206, the computer 16 sets a neighboring pixel above target pixel as a new target pixel. The program then returns to Step 182 so as to perform the above-described processes against the new target pixel.

As described above, through the implementation of the edge-characterizing point detection routine, an edge-characterizing point Pi (i=0, 1, . . . ), of which edge value is positive, and an edge-characterizing point(s) Mi (i=0, 1, . . . ), of which edge value is negative, are detected on the same.

In Step 112 of the image processing routine illustrated in FIG. 3, the computer 16 controls the eyelid boundary point detecting portion 26 to detect the first boundary point between the upper eyelid and the eyeball based upon the edge-characterizing point Pi and to detect the second boundary point between the lower eyelid and the eyeball based upon the edge-characterizing point Mi.

When the eyelid boundary point detecting portion 26 detects plural edge-characterizing points Pi and Mi respectively, the first boundary point and the second boundary point are each detected as described below in Step 112.

First, the eyelid boundary point detecting portion 26 allows a search window to move within an image on which multiple edge-characterizing points Pi are plotted, so that a first boundary point is detected. The search window can be determined based upon a range of picture elements for the upper eyelid, which range is derived for example experimentally in advance. The search window can have for example 1 pixel vertically and 15 pixels horizontally (1×15), and the pixel size of the search window is determined appropriately in response to resolution, scaling or the like. More specifically, the eyelid boundary point detecting portion 26 calculates a sum of pixel intensities of edge-characterizing points Pi forming a transverse edge in the search window while moving the search window in the image on which multiple edge-characterizing points Pi are plotted. The eyelid boundary point detecting portion 26 then identifies the edge-characterizing point for the transverse edge (an edge changed from white to black) appearing in the search window moved to an area which satisfies a condition that a sum of pixel intensities of the edge-characterizing points Pi for the corresponding transverse edge therein reaches a predetermined value, as "a candidate for the first boundary point between the upper eyelid and the eyeball". In this case, in the event where multiple candidates for the first boundary point appear adjacent to each other in an up-down direction in the image, candidate(s), which is not a point (candidate) located uppermost, is to be cleared. Further, in the event where a candidate for the first boundary point appears near the upper end of an eye window, the candidate is to be cleared. This is because a transverse edge for an eyebrow may occasionally appear near the upper end of the eye window. After clearing the candidate appearing near the upper end of the eye window, the eyelid boundary point detecting portion 26 detects a candidate for the first boundary point remaining in the eye window as the first boundary point between the upper eyelid and the eyeball.

Alternatively, a first boundary point between an eyelid and an eyeball can be extracted based upon the shape of the eyelid that is arc shaped when the eye is open. That is, continuous edges, each of which changes from white to black in the vertical direction, extending in an arc shape approximately in a horizontal direction can be recognized as edges forming the first boundary point between the upper eyelid and the eyeball. By making use of the shape feature of the eyelid as described above, it is possible to detect a first boundary point between an upper eyelid and an eyeball with high detection precision. Further, when multiple and continuous image frames are employed, a first boundary point between an upper eyelid and an eyeball can be determined with reference to the characteristic that the upper eyelid is likely to move wider than other neighboring portions, such as a lower eyelid, an eyebrow, a frame of eyeglasses, when blinking.

A search window, which is employed to detect a second boundary point between a lower eyelid and the eyeball, is positioned based upon the position of the first boundary point. More specifically, the search window for the second boundary point is set at a lower side of the position of the first boundary point, with reference to the position of the first boundary point detected as described above. For example, the search window for the second boundary point can be set at a lower side than the position of the first boundary point by the number of picture elements, which corresponds to an average size of an eye, i.e., an average distance between the upper eyelid and the lower eyelid when the eye is in an open state. The size of the search window for the second boundary point can be substantially equal to that of the search window for the first boundary point. The size of the search window for the second boundary point can be determined based upon a range of picture elements for the lower eyelid, which range is extracted in advance for example through experiments.

The search window to detect the second boundary point is moved to a position determined in an image on which multiple edge-characterizing points Mi are plotted, so that the second boundary point between the lower eyelid and the eyeball is detected. For example, in a case where edge-characterizing point Mi for a transverse edge (an edge changed from black to white) appears in the search window for the second boundary point, the edge-characterizing point Mi is detected as the second boundary point between the lower eyelid and the eyeball.

Alternatively, in Step 112, a boundary point may be detected based upon an edge value at an edge-characterizing point. For example, an edge value of an edge-characterizing point, which is plotted due to shadow, is likely to be small, so that an edge-characterizing point exhibiting an edge value being greater than, or equal to, a predetermined value can be recognized as a candidate for a boundary point so as to detect a boundary point.

In Step 114, the controller 16 controls the eyelid-opening measuring portion 28 to measure a distance between the first boundary point and the second boundary point. The distance is outputted as an eyelid-opening to the display unit 18, and the image processing routine is completed.

Figure 9A:
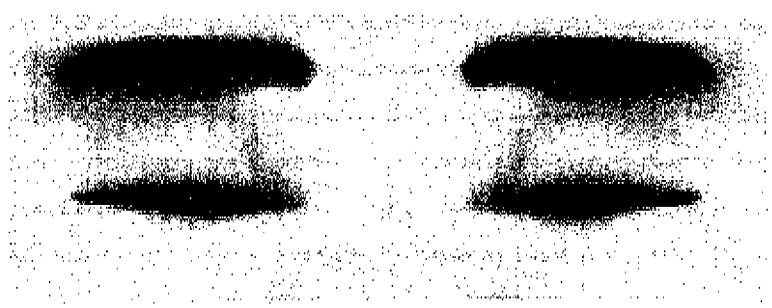
FIG. 9A is diagram illustrating an eye image including eyes which are in a closed state and eyelids are applied with eye shadow.
Figure 9B:
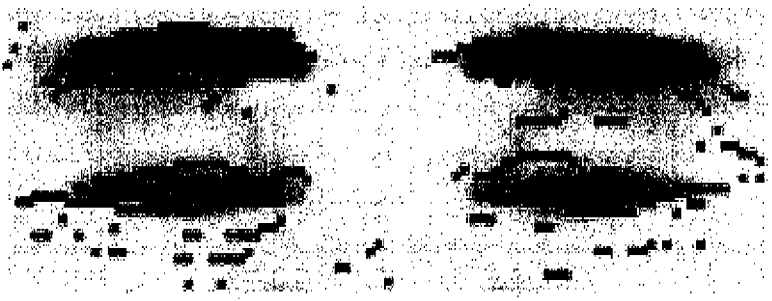
FIG. 9B is a diagram illustrating a local maximal value point and a local minimal value point detected in a Sobel edge image based upon the eye image in FIG. 9A.
Figure 9C:
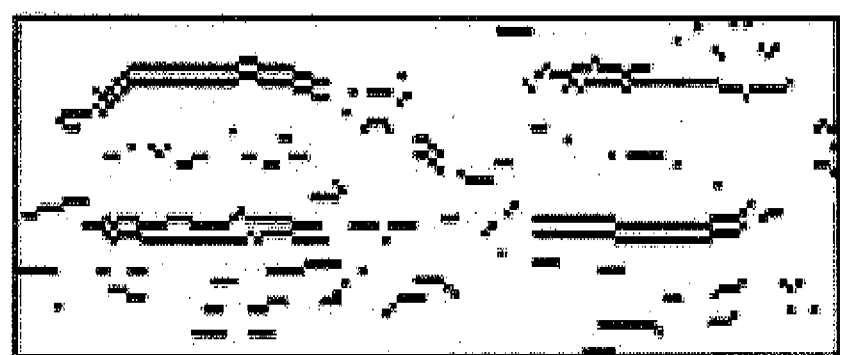
FIG. 9C is a diagram illustrating edge-characterizing points plotted in the Sobel edge image.
Figure 9D:
FIG. 9D is a diagram illustrating boundary points of an eyelid based upon the edge-characterizing points in FIG. 9C.
Figure 10B:
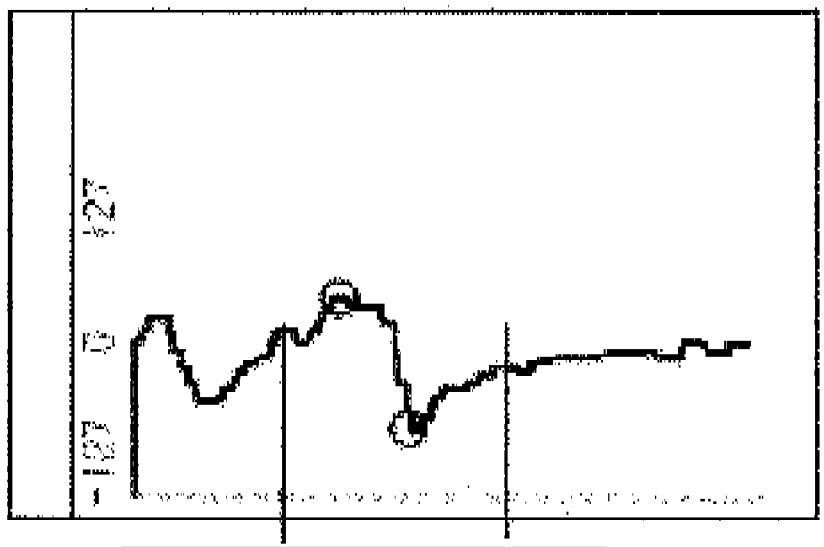
FIG. 10B is a graph summarizing changes in edge values in the Sobel edge image in FIG. 10A.
Figure 10A:
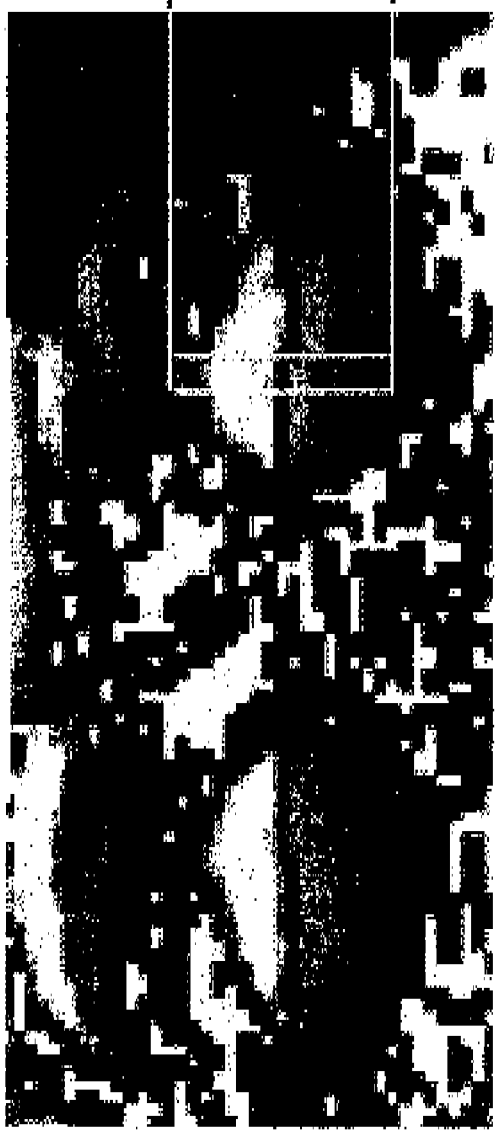
FIG. 10A is a diagram illustrating a Sobel edge image generated based upon an eye image including eyes which are in a closed state and is applied with eye shadow.

Through the implementations of the image processing routine described above, in a case where an eyelid is applied with eye shadow and the eye is in a closed state as illustrated in FIG. 9A, the edge processing with a Sobel filter generates a Sobel edge image illustrated in FIG. 10A. In this case, as illustrated in FIGS. 9B and 10B, the gradient of edge value at or around a local maximal value point is not steep but flat. Further, even when the local maximal value point and the local minimal value point are plotted distant from corresponding boundary points of the eyelid respectively, it is possible to detect a point close to the corresponding boundary point of an eyelid as an edge-characterizing point, as illustrated in FIG. 9C. Therefore, as illustrated in FIG. 9D, the boundary points of an eyelid are detected with high detection precision.

Figure 11A:
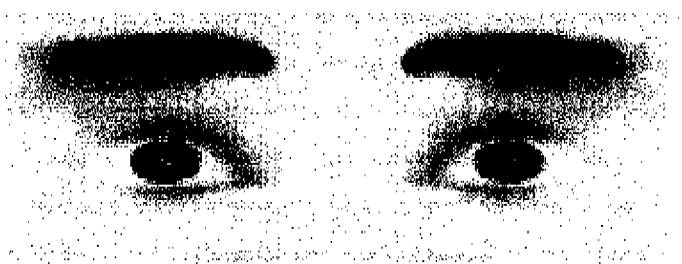
FIG. 11A is diagram illustrating an eye image including eyes which are in an open state and is applied with eye shadow.
Figure 11B:
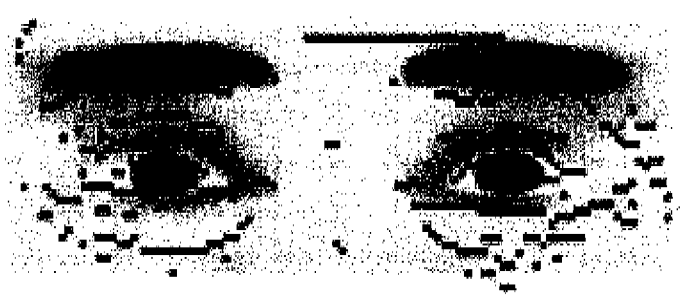
FIG. 11B is a diagram illustrating a local maximal value point and a local minimal value point detected in a Sobel edge image based upon the eye image in FIG. 11A.
Figure 11C:
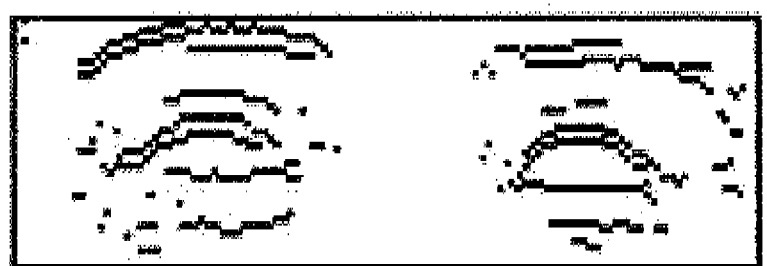
FIG. 11C is a diagram illustrating edge-characterizing points plotted in the Sobel edge image.
Figure 11D:
FIG. 11D is a diagram illustrating boundary points of an eyelid based upon the edge-characterizing points in FIG. 11C.

On the other hand, in a case where an eyelid is applied with eye shadow and the eye is in an open state as illustrated in FIG. 11A, the local maximal value point and the local minimal value point are plotted close to corresponding boundary points of the eyelid respectively, (see FIG. 11B) and a point close to the boundary point of an eyelid is detected as an edge-characterizing point (see FIG. 11C). Therefore, as illustrated in FIG. 11D, boundary points of the eyelid are detected with high detection precision.

As described above, according to the first embodiment, the computer 16 detects a point, which is shifted from a local maximal value point having an edge value being a local maximal value in an up-down direction heading towards an eyeball, has an edge value (corresponding to the predetermined value) being smaller by a set value than the local maximal value, and is positioned closest to the local maximal value point from among points respectively having the edge values being smaller by the set value than the local minimal value, as an edge-characterizing point. The computer 16 further detects a point, which is shifted from a local minimal value point having an edge value being a local minimal value in a down-up direction heading towards an eyeball, has an edge value (corresponding to the predetermined value) being smaller by a set value than the local minimal value, and is positioned closest to the local minimal value point from among points respectively having the edge values being smaller by the set value than the local minimal value. The computer 16 then detects a boundary point of an upper eyelid based upon the edge-characterizing point at an upper side of the eyeball and detects a boundary point of a lower eyelid based upon the edge-characterizing point at a lower side of the eyeball. Therefore, even where an eye is applied with eye shadow, it is possible to detect a boundary point between an eyelid and an eyeball with high detection precision.

Further, because a boundary point(s) of an eyelid and an eyeball is detected accurately, an eyelid-opening is measured with high precision.

According to the first embodiment, an edge image, which represents a magnitude of grayscale change, is generated based upon a grayscale image inputted into the image input portion 20. An image inputted into the image input portion 20 can be however a color image. In this case, an edge image to be generated represents a magnitude of concentration change of the color image.

According to the first embodiment, an edge-characterizing point, which is shifted from a local maximal value point towards an eyeball, is detected as a boundary point of an upper eyelid, and an edge-characterizing point, which is shifted from a local minimal value point towards the eyeball, is detected as a boundary point of a lower eyelid. Alternatively, for example in a case where an eye image includes a bright eyeball and dark skin around the eyeball, an edge-characterizing point, which is shifted from a local maximal value point towards the eyeball, can be detected as a boundary point of a lower eyelid, and an edge-characterizing point, which is shifted from a local minimal value point towards the eyeball, can be detected as a boundary point of an upper eyelid.

According to the first embodiment, the computer 16 controls the ROM to store an edge value at an edge-characterizing point as well as the edge-characterizing point when storing the edge-characterizing point. Alternatively, the computer 16 can control the ROM to store a local maximal value point, or a local minimal value point, which is located close to an edge-characterizing point, as well as the edge-characterizing point when storing the edge-characterizing point.

According to the first embodiment, in the event where multiple edge-characterizing points are detected for each of the first and second boundary points, search windows are employed to detect the first and second boundary points, respectively. Alternatively, the computer 16 can examine multiple edge-characterizing points connected to each other and establish a group of the edge-characterizing points. A mean position of the group can be detected as a first boundary point or a second boundary point.

Described below is an eyelid detection apparatus according to a second embodiment. The structure of the eyelid detection apparatus of the second embodiment is substantially the same as that of the first embodiment, so that the same element is attached with the same reference numeral.

Detection of an edge-characterizing point according to the second embodiment is different from that according to the first embodiment in which, according to the second embodiment, a point, which is shifted from a local maximal value point (corresponding to the local peak value point) in an up-down direction towards an eyeball, has an edge vale being equal to a predetermined set value (the edge value corresponding to the predetermined value), and is closest to the local maximal value point from among points respectively having the edge values being equal to the predetermined set value, is detected as an edge-characterizing point.

Figure 12:
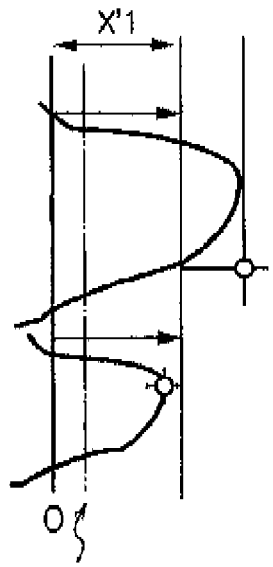
FIG. 12 is a diagram for explaining an edge-characterizing point detected through an edge-characterizing point detection routine according to a second embodiment.

According to the second embodiment, when an edge value is positive through an edge-characterizing point detection routine, the computer 16 examines each picture element from up to down and finds a picture element exhibiting an edge value being a local maximal value. When the local maximal value has been stored in the RAM, the computer 16 judges two conditions, whether an edge value of a neighboring pixel above a target pixel (one pixel above the target pixel), which is not the target pixel, is greater than a set value $X'1$ ($X'1>0$) and whether an edge value of the target pixel is less than, or equal to, the set value $X'1$. When an affirmative answer "Yes" is obtained, i.e., when the computer 16 determines that an edge value of the neighboring pixel above the target pixel is greater than the set value $X'1$ ($X'1>0$) and that the edge value of the target pixel is less than, or equal to, the set value $X'1$, the computer 16 determines that the target pixel is a point closer to the dark side (area) in the variation (bright to dark) of pixel intensity value in the up-down direction, which point has an edge value being equal to the set value $X'1$ (the edge value corresponding to the predetermined value) and is closest to a local maximal value point from among points respectively having the edge values being equal to the set value $X'1$, as illustrated in FIG. 12. The computer 16 ten recognizes the position of the target pixel as an edge-characterizing point and clears the local maximal value already stored in the RAM.

The set value $X'1$ is defined by experimentally or statistically obtaining an edge value at a boundary point of an upper eyelid in the event that the eyelid is applied with eye shadow and by determining the edge value obtained as the set value $X'1$.

When an edge value is negative through an edge-characterizing point detection routine, the computer 16 examines each picture element from down to up and finds a picture element exhibiting an edge value being a local minimal value. When the local minimal value has been stored in the RAM, the computer 16 judges two conditions, whether an edge value of a neighboring pixel below a target pixel (one pixel below the target pixel), which is not the target pixel, is smaller tan a set value $X'2$ ($X'2<0$) and whether the edge value of the target pixel is greater than, or equal to, the set value $X'2$. When an affirmative answer "Yes" is obtained, i.e., when the computer 16 determines that an edge value of the neighboring pixel below the target pixel is smaller than the set value $X'2$ and that the edge value of the target pixel is greater than, or equal to, the set value $X'2$, the computer 16 determines that the target pixel is a point closer to the dark side (area) in the variation (dark to bright) of pixel intensity value in the up-down direction, which point has an edge value being equal to the set value $X'2$ (the edge value corresponding to the predetermined value) and is closest to a local minimal value point (corresponding to the local peak value point) from among points respectively having the edge values being equal to the set value $X'2$. The computer 16 then recognizes the position of the target pixel as an edge-characterizing point and clears the local minimal value already stored in the RAM.

The set value $X'2$ is defined by experimentally or statistically obtaining an edge value at a boundary point of a lower eyelid in the event that the eyelid is applied with eye shadow and by determining the edge value obtained as the set value $X'2$.

As described above, according to the second embodiment, the computer 16 detects, in a Sobel edge image having an eye image, a point, which is shifted from a local maximal value point having an edge value being the local maximal value in an up-down direction heading towards an eyeball, has an edge value (corresponding to the predetermined value) being equal to a set value, and is positioned closest to the local maximal value point from among points respectively having the edge values being equal to the set value, as an edge-characterizing point. The computer 16 further detects a point, which is shifted from a local minimal value point having an edge value being the local minimal value in a down-to-up direction heading towards the eyeball, has an edge value being equal to a set value (the edge value corresponding to the predetermined value), and is closest to the local minimal value point from among points respectively having the edge values being equal to the set value, as an edge-characterizing point. The computer 16 then detects boundary points of an eyelid based upon the edge-characterizing points detected as described above. Therefore, even when an eye is applied with eye shadow, it is possible to detect a boundary point between an eyelid and an eyeball with high detection precision.

Described below is an eyelid detection apparatus according to a third embodiments. The structure of the eyelid detection apparatus of the third embodiment is substantially the same as that of the first embodiment, so that the same element is attached with the same reference numeral.

Detection of an edge-characterizing point according to the third embodiment is different from that according to the first embodiment in which, according to the third embodiment, a point, which is shifted from a local maximal value point (corresponding to the local peak value point) in an up-down direction towards an eyeball, has an edge value being equal to a value obtained by subtracting a first threshold value D1 (corresponding to a set value) from a magnitude of pixel value change at the local maximal value point, by multiplying the subtraction result (a second value) with a predetermined set ratio, and by subtract the multiplication result (a first value) from the local maximal value, and is closest to the local maximal value point from among points respectively having the edge values being equal to the value obtained described above (the edge value corresponding to the predetermined value), is detected as an edge-characterizing point.

Figure 13:
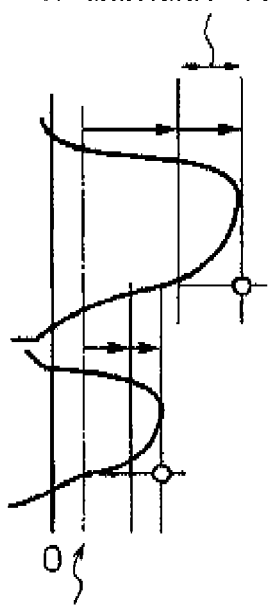
FIG. 13 is a diagram for explaining an edge-characterizing point detected through an edge-characterizing point detection routine according to a third embodiment.

According to the third embodiment, when an edge value is positive through the edge-characterizing point detection routine, the computer 16 examines each picture element from up to down and finds a pixel exhibiting an edge value being a local maximal value. When the local maximal value has been stored in the RAM, the computer 16 judges two conditions, whether edge value of a neighboring pixel above a target pixel (one pixel above the target pixel), which is not the target pixel, is greater than (local maximal value–(local maximal value–D1)×set ratio A1) and whether an edge value of the target pixel is less than, or equal to, (local maximal value–(local maximal value–D1)×set ratio A1). When an affirmative answer "Yes" is obtained, i.e., when the computer 16 determines that an edge value of the neighboring pixel above the target pixel, which is not the target pixel, is greater than (local maximal value–(local maximal value–D1)×set ratio A1) and that the edge value of the target pixel is less than, or equal to, (local maximal value–(local maximal value–D1)×set ratio A1), the computer 16 determines that the target pixel is a point closer to the dark side (area) in the variation (bright to dark) of pixel intensity value in the up-down direction, which point has an edge value being equal to (local maximal value–(local maximal value–D1)×set ratio A1) and is positioned closest to a local maximal value point (corresponding to the local peal, value point) from among points respectively having the edge values being equal to (local maximal value–(local maximal value–D1)×set ratio A1), as illustrated in FIG. 13. The computer 16 then recognizes the position of the target pixel as an edge-characterizing point and clears the local maximal value already stored in the RAM.

The set ratio A1 is defined by experimentally or statistically obtaining an edge value at a boundary point of an upper eyelid in the event that the eyelid is applied with eye shadow and by obtaining a ratio of a difference between a local maximal value and the edge value obtained relative to a difference between the local maximal value and the first threshold value D1 (corresponding to a set value). That is, the ratio is pre-set as the set ratio A1.

When an edge value is negative through the edge-characterizing point detection routine, the computer 16 examines each picture element from down to up and finds a picture element exhibiting an edge value being a local minimal value. When the local minimal value has been stored in the RAM, the computer 16 judges two conditions, whether an edge value of a neighboring pixel below a target pixel (one pixel below the target pixel), which is not the target pixel, is smaller than (local minimal value–(local minimal value–D2)×set ratio A2) ad whether an edge value of the target pixel is greater than, or equal to, (local minimal value–(local minimal value–D2)×set ratio A2). When an affirmative answer "Yes" is obtained, i.e., when the computer 16 determines that an edge value of the neighboring pixel below the target pixel, which is not the target pixel, is smaller than (local minimal value–(local minimal value–D2)×set ratio A2) and that the edge value of the target pixel is greater than, or equal to, (local minimal value–(local minimal value–D2)×set ratio A2), the computer 16 determines that the target pixel is a point closer to the dark side (area) in the variation (dark to bright) of pixel intensity value in the up-down direction, which point has an edge value being equal to (local minimal value–(local minimal value–D2)×set ratio A2) and is positioned closest to a local minimal value point (corresponding to the local peak value point) from among points respectively having the edge values being equal to (local minimal value–(local minimal value–D1)×set ratio A2). The computer 16 then recognizes the position of the target pixel as an edge-characterizing point and clears the local minimal value already stored in the RAM.

The set ratio A1 is defined by experimentally or statistically obtaining an edge value at a boundary point of an upper eyelid in the event that the eyelid is applied with eye shadow and by obtaining a ratio of a difference between a local maximal value and the edge value obtained relative to a difference between the local maximal value and the second threshold value D2 (corresponding to the set value). That is, the ratio is pre-set as the set ratio A1.

As described above, according to the Bird embodiment, the computer 16 detects, in a Sobel edge image having an eye image, a point, which is shifted from a local maximal value point having an edge value being a local maximal value in an up-down direction heading towards an eyeball, has an edge value (corresponding to the predetermined value) being equal to (local maximal value–(local maximal value–set value)×set ratio), and is closest to the local maximal value point from among points respectively having the edge values being equal to (local maximal value–(local maximal value–set value)×set ratio), as an edge-characterizing point. The computer 16 further detects, in the Sobel edge image having the eye image, a point, which is shifted from a local minimal value point having an edge value being a local minimal value in a down-up direction heading towards the eyeball, has an edge value (corresponding to the predetermined value) being equal to (local minimal value–(local minimal value–set value)×set ratio), and is closest to the local minimal value point from among points respectively having the edge values being equal to (local minimal value–(local minimal value–set value)×set ratio), as an edge-characterizing point. The computer 16 then detects a boundary point of an upper eyelid based upon the edge-characterizing point obtained at an upper side of be eyeball and detects a boundary point of the lower eyelid based upon the edge-characterizing point at a lower side of the eyeball. Therefore, even where an eye is applied with eye shadow, it is possible to detect a boundary point between an eyelid and an eyeball with high detection precision.

Described below is an eyelid detection apparatus according to a fourth embodiment. The structure of the eyelid detection apparatus of the fourth embodiment is substantially the same as that of the first embodiment, so that the same element is attached with the same reference numeral.

Detection of an edge-characterizing point according to the fourth embodiment is different from that according to the first embodiment in which, according to the fourth embodiment, a point, which is shifted from a local maximal value point (corresponding to the local peak value point) in up-down direction has a change ratio of its edge value being a local maximal value, and is closest to the local maximal value point from among points respectively having the change ratios being the local maximal value.

Figure 14:
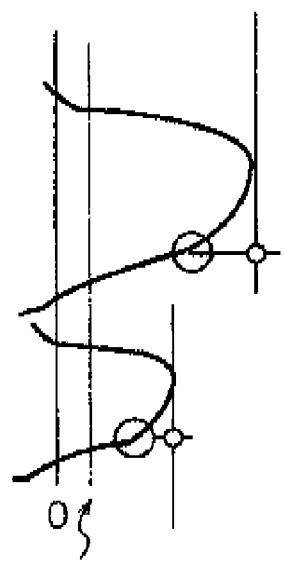
FIG. 14 is a diagram for explaining an edge-characterizing point detected through an edge-characterizing point detection routine according to a fourth embodiment.

According to the fourth embodiment, when an edge value is positive through an edge-characterizing point detection routine, the computer 16 examines each picture element from up to down and finds a picture element having an edge value being a local maximal value. When the local maximal value has been stored in the RAM, the computer 16 calculates change ratio of edge values of a target pixel (having an edge value not being the local maximal value), a neighboring pixel above the target pixel (one pixel above the target pixel), and a neighboring pixel below the target pixel (one pixel below the target pixel). The computer 16 then judges whether two conditions are satisfied, two conditions being that the edge value of the neighboring pixel above the target pixel is greater than the edge value of the target pixel and that a change ratio of the edge value of the target pixel is the local maximal value. When an affirmative answer "Yes" is obtained based upon the change ratios of the edge values of the neighboring pixel above the target pixel, the target pixel and the neighboring pixel below the target pixel, i.e., when the computer 16 determines that the change ratio of edge value of the target pixel is the local maximal value and that the edge value of the neighboring pixel above the target pixel is greater than that of the target pixel, the computer 16 determines that the target pixel is a point closer to the dark side (area) in the variation (bright to dark) of pixel intensity value in the up-down direction, which point has an edge value change ratio being the local maximal value, and is closest to a local maximal value point from among points respectively having the edge value change-ratios being the local maximal value, as illustrated in FIG. 14. The computer 16 then recognizes the position of the target pixel as an edge-characterizing point and clears the local maximal value already stored in the RAM.

When an edge value is negative through the edge-characterizing point detection routine, the computer 16 examines each picture element from down to up and finds a picture element exhibiting an edge value being a local minimal value. When the local minimal value has been stored in the RAM, the computer 16 calculates change ratios of edge values of a target pixel (the edge value not being the local minimal value), a neighboring pixel below the target pixel (one pixel below the target pixel) and a neighboring pixel above the target pixel (one pixel above the target pixel). The computer 16 then judges whether two conditions are satisfied, two conditions being that the edge value of the neighboring pixel below the target pixel is smaller than the edge value of the target pixel and that a change ratio of the edge value of the target pixel is a local maximal value. When an affirmative answer "Yes" is obtained based upon the change ratios of the edge values of the neighboring pixel above the target pixel, the target pixel and the neighboring pixel below the target pixel, i.e., when the computer 16 determines that the change ratio of edge value of the target pixel is a local maximal value and that the edge value of the neighboring pixel below the target pixel is smaller than that of the target pixel, the computer 16 (determines that the target pixel is a point closer to the dark side (area) in the variation (dark to bright) of pixel intensity value in the up-down direction, which point has an edge value change ratio being the local maximal value, and is closest to a local minimal value point from among points respectively having the edge value change ratios being the local maximal value. The computer 16 then recognizes the position of the target pixel as an edge-characterizing point and clears the local maximal value already stored in the RAM.

As described above, according to the fourth embodiment, the computer 16 detects, in a Sobel edge image having an eye image, a point, which is shifted from a local maximal value point having an edge value being the local maximal value in an up-down direction heading towards an eyeball, has an edge value change ratio being a local maximal value, and is positioned closest to a local maximal value point (corresponding to the local peak value point) from among points respectively having the edge value change ratios being the local maximal value, as an edge-characterizing point. The computer 16 further detects, in the Sobel edge image, a point, which is shifted from a local minimal value point having an edge value change ratio being the local maximal value in a down-to-up direction heading towards the eyeball, has an edge value change ratio being a local maximal value, and is positioned closest to a local minimal value point (corresponding to the local peak value point) from among points respectively having the edge value change ratios being the local maximal value, as an edge-characterizing point. The computer 16 then detects boundary points based upon the edge-characterizing points detected as described above. Therefore, even when an eye is applied with eye shadow, it is possible to detect a boundary point between an eyelid and an eyeball with high detection precision.

Described below is an eyelid detection apparatus according to a fifth embodiment. The structure of the eyelid detection apparatus of the fifth embodiment is different from that of the first embodiment in that, according to the fifth embodiment, the apparatus does not include the edge-characterizing point detecting portion 24 but includes a pixel value non-changing point detecting portion. Further, an image processing routine of the fifth embodiment includes a pixel value non-changing point detecting process in substitution for the edge-characterizing detecting process (Step 110) of the image processing routine of the first embodiment.

Figure 15:
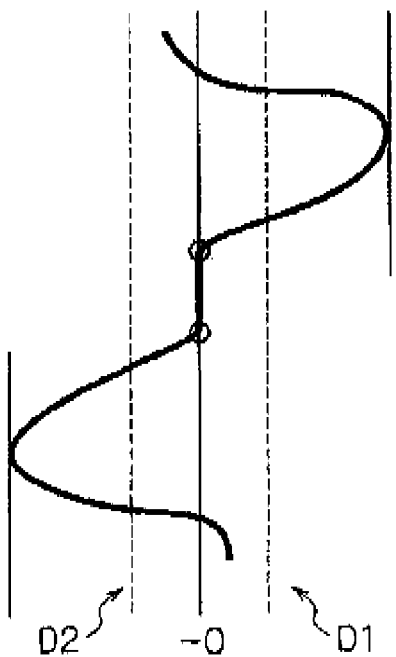
FIG. 15 is a diagram for explaining a point where changes in pixel intensity value reaches zero according to a fifth embodiment.

FIG. 15 is a diagram for explaining a point where a change of pixel value reaches zero according to the fifth embodiment.

According to the fifth embodiment, when the computer 16 judges that an edge value is positive, the computer 16 detects, as a first boundary point indicating a boundary between an upper eyelid and an eyeball, a point, which is shifted from a local maximal value point in an up-down direction towards an eyeball and where a change in pixel intensity value does not exist (reaches approximately zero).

The pixel value non-changing point detecting portion of the fifth embodiment detects a point, where a change in pixel value reaches approximately zero first towards the eyeball from the local maximal value point (the pixel value non-changing point detecting process). The eyelid boundary detecting portion 26 detects this point as the first boundary point.

In the same manner, when the computer 16 judges that an edge value is negative, the computer 16 detects, as a second boundary point indicating a boundary between a lower eyelid and the eyeball, a point, which is shifted from a local minimal value point in an down-up direction towards the eyeball and where a change in pixel intensity value does not exist (reaches approximately zero).

The pixel value non-changing point detecting portion of the fifth embodiment detects a point, where a change in pixel value reaches approximately zero first towards the eyeball from the local minimal value point (the pixel value non-changing point detecting process). The eyelid boundary detecting portion 26 detects this point as the second boundary point.

Detection of the first and second boundary points as described above enables to detect a boundary point between an eyelid and an eyeball with high detection precision and to measure an eyelid-opening with high precision.

The computer 16, i.e., the edge-characterizing point detecting portion 24 (corresponding to edge image generating means) generates an edge image representing a magnitude of pixel value change per pixel in a predetermined direction in a region including an eye, based upon an image of the region. The computer 16, i.e., the edge-characterizing point detecting portion 24 (corresponding to local peak value point searching means) searches a local peak value point, where the magnitude of pixel value change reaches a local peak value in the predetermined direction, in the edge image generated by the edge image generating means. The computer 16, i.e., the eyelid boundary point detecting portion 26 (corresponding to boundary point detecting means) detects at least one of a first boundary point indicating a boundary between an upper eyelid and an eyeball and a second boundary point indicating a boundary between a lower eyelid and the eyeball, based upon a point which is shifted from the local peak value point searched by the eyelid boundary point detecting portion 26 in a direction towards the eyeball.

As described above, in an edge image, a boundary point is detected based upon a point shifted towards the eyeball from a local peak value point having a magnitude of pixel value change being a local peak value. Therefore, even when an eyelid is colored such as eye shadow, it is possible to detect a boundary point between the eyelid and the eyeball with high detection precision.

The point, which is shifted from the local peak value point in the direction towards the eyeball, has the magnitude of pixel value change being a predetermined value and is positioned closest to the local peak value point from among points respectively having magnitudes of pixel value change being the predetermined value, and wherein the eyelid boundary point detecting portion 26 detects the at least one of the first boundary point and the second boundary point based upon the point closest to the local peak value point. Therefore, it is possible to detect a point, which has a magnitude of pixel value change being a predetermined value corresponding to a magnitude of pixel value at a boundary point and is positioned closest to a local peak value point.

It is preferable that the predetermined value is smaller by a set value than the magnitude of pixel value change of the local peak value point. As described above, it is possible to employ, as the predetermined value corresponding to a magnitude of pixel value change at a boundary point, a value smaller by the predetermined set value than the magnitude of pixel value change of the local peak value point.

It is further preferable that the predetermined value is a set value. As described above, it is possible to employ, as the predetermined value corresponding to a magnitude of pixel value change at a boundary point, a value being the predetermined set value.

It is still further preferable that the predetermined value is obtained by subtracting a first value, which is obtained by multiplying by a predetermined set ratio a second value obtained by subtracting a set value from the magnitude of pixel value change of the local peak value point, from the magnitude of pixel value change of the local peak value point. As described above, it is possible to employ, as the predetermined value corresponding to a magnitude of pixel value change of the local peak value point, a value obtained based upon a magnitude of pixel value change of the local peak value point, the predetermined set value, and the predetermined set ratio.

It is preferable the point, which is shifted from the local peak value point in the direction towards the eyeball, has a change ratio of the magnitude of pixel value change in the predetermined direction being a local peak value in the predetermined direction, and is positioned closest to the local peak value point. The eyelid boundary point detecting portion 26 detects the at least one of the first boundary point and the second boundary point based upon the point. As described above, it is possible to detect, as a boundary point between an eyelid and an eyeball, a point having a change ratio of a magnitude of pixel value change being a local peak value and positioned closest to a local peak value point from among points respectively having change ratios of magnitude of pixel value change being a local peak value.

It is preferable that the predetermined direction is a blinking direction. Accordingly, it is possible to describe an edge of a boundary of an eyelid and a boundary with us of a pixel value change in the blinking direction in the edge image.

It is further preferable that the point, which is shifted from the local peak value point in the direction towards the eyeball is a point where a pixel value change does not exist, and the eyelid boundary point detecting portion 26 detects the at least one of the first boundary point and the second boundary point based upon the point. Accordingly, it is possible to detect the point, where the pixel value change disappears, as a boundary point between an eyelid and an eyeball.

As described above, according to the eyelid detection apparatus and program therefor, in an edge image, a boundary point is detected based upon a point shifted from a local peak value point, of which magnitude of pixel value change reaches a local peak value, in a direction towards an eyeball. Therefore, an effect is obtained, in which a boundary point between an eyelid and the eyeball is detected accurately even when the eyelid is colored.

The principles, preferred embodiments and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. An eyelid detection apparatus comprising:
    a generating means for generating an edge image representing a magnitude of pixel value change per pixel in a predetermined direction in a region including an eye, based upon an image of the region including the eye;
    a local peak value point searching means for searching a local peak value point, where the magnitude of pixel value change reaches a local peak value in the predetermined direction, in the edge image generated by the generating means; and
    a boundary point detecting means for detecting at least one of a first boundary point indicating a boundary between an upper eyelid and an eyeball and a second boundary point indicating a boundary between a lower eyelid and the eyeball, based upon a point which is shifted from the local peak value point searched by the local peak value point searching means in a direction towards the eyeball and which is closest to the local peak value point so that the magnitude of the pixel value change becomes a value smaller than the magnitude of the pixel value change at the local peak value point by a preliminarily set value.

2. An eyelid detection apparatus according to claim 1, wherein the preliminarily set point is set as a difference between the pixel value change at the local peak value point, which is preliminarily obtained, on the one hand and at least one of the pixel value change at the first boundary point indicating the boundary between the upper eyelid and the eyeball and the pixel value change at the second boundary point indicating the boundary between the lower eyelid and the eyeball on the other hand.

3. An eyelid detection apparatus according to any claim 2, wherein the predetermined direction is a blinking direction.

4. An eyelid detection apparatus according to claim 1, wherein the predetermined direction is a blinking direction.

5. An eyelid detection apparatus comprising:
a generating means for generating an edge image representing a magnitude of pixel value change per pixel in a predetermined direction in a region including an eye, based upon an image of the region including the eye;
a local peak value point searching means for searching a local peak value point, where the magnitude of pixel value change reaches a local peak value in the predetermined direction, in the edge image generated by the generating means; and
a boundary point detecting means for detecting at least one of a first boundary point indicating a boundary between an upper eyelid and an eyeball and a second boundary point indicating a boundary between a lower eyelid and the eyeball, based upon a point which is shifted from the local peak value point searched by the local peak value point searching means in a direction towards the eyeball and which is closest to the local peak value point so that the magnitude of the pixel value change becomes a value obtained by subtracting a value, which is calculated by multiplying the magnitude of the pixel value change at the local peak value point by a predetermined ratio, from the magnitude of the pixel value change at the local peak value point.

6. An eyelid detection apparatus according to claim 5, wherein the local peak value point searching means searches the local peak value point at which the magnitude of the pixel value change reaches the local peak value in the predetermined direction and at which the pixel value change becomes equal to or greater than a preliminarily set threshold value, in the edge image generated by the generating means, the predetermined ratio is set as ratio of a difference between the pixel value change at the local peak value point on the one hand and at least one of the pixel value change at the first boundary point indicating the boundary between the upper eyelid and the eyeball and the pixel value change at the second boundary point indicating the boundary between the lower eyelid and the eyeball on the other hand relative to a difference between the pixel value change at the local peak value point and the threshold value, which is preliminarily obtained.

7. An eyelid detection apparatus according claim 6, wherein the predetermined direction is a blinking direction.

8. An eyelid detection apparatus according to claim 5, wherein the predetermined direction is a blinking direction.

9. An eyelid detection apparatus comprising:
a generating means for generating an edge image representing a magnitude of pixel value change per pixel in a predetermined direction in a region including an eye, based upon an image of the region including the eye;
a local peak value point searching means for searching a local peak value point, where the magnitude of pixel value change reaches a local peak value in the predetermined direction, in the edge image generated by the generating means; and
a boundary point detecting means for detecting at least one of a first boundary point indicating a boundary between an upper eyelid and an eyeball and a second boundary point indicating a boundary between a lower eyelid and the eyeball, based upon a point which is shifted from the local peak value point searched by the local peak value point searching means in a direction towards the eyeball and which is closest to the local peak value point so that the magnitude of the pixel value change becomes a value obtained by subtracting a value, which is calculated by subtracting a preliminarily set value from the magnitude of the pixel value change at the local peak value point and then multiplying the obtained value by a predetermined ratio, from the magnitude of the pixel value change at the local peak value point.

10. An eyelid detection apparatus according to claim 9, wherein the local peak value point searching means searches the local peak value point at which the magnitude of the pixel value change reaches the local peak value in the predetermined direction and at which the pixel value change becomes equal to or greater than a preliminarily set threshold value in the edge image generated by the generating means, the predetermined ratio is set as a ratio of a difference between the pixel value change at the local peak value point on the one hand and at least one of the pixel value change at the first boundary point indicating the boundary between the upper eyelid and the eyeball and the pixel value change at the second boundary point indicating the boundary between the lower eyelid and the eyeball on the other hand relative to a difference between the pixel value change at the local peak value point and the threshold value, which is preliminarily obtained, and the preliminarily set value is set as the threshold value.

11. An eyelid detection apparatus according to claim 10, wherein the predetermined direction is a blinking direction.

12. An eyelid detection apparatus according to claim 9, wherein the predetermined direction is a blinking direction.

13. A non-transitory computer readable medium including a program operating a computer to execute a method, the method comprising:
generating an edge image representing a magnitude of pixel value change per pixel in a predetermined direction in a region including an eye, based upon an image of the region including the eye;
searching a local peak value point, where the magnitude of pixel value change reaches a local peak value in the predetermined direction, in the edge image generated by the generating means; and
detecting at least one of a first boundary point indicating a boundary between an upper eyelid and an eyeball and a second boundary point indicating a boundary between a lower eyelid and the eyeball, based upon a point which is shifted from the local peak value point searched by the local peak value point searching means in a direction towards the eyeball and which is closest to the local peak value point so that the magnitude of the pixel value change becomes a value smaller than the magnitude of the pixel value change at the local peak value point by a preliminarily set value.

14. A non-transitory computer readable medium including a program operating a computer to execute a method, the method comprising:
generating an edge image representing a magnitude of pixel value change per pixel in a predetermined direction in a region including an eye, based upon an image of the region including the eye;
searching a local peak value point, where the magnitude of pixel value change reaches a local peak value in the predetermined direction, in the edge image generated by the generating means; and
detecting at least one of a first boundary point indicating a boundary between an upper eyelid and an eyeball and a second boundary point indicating a boundary between a lower eyelid and the eyeball, based upon a point which is shifted from the local peak value point searched by the local peak value point searching means in a direction towards the eyeball and which is closest to the local peak value point so that the magnitude of the pixel value change becomes a value obtained by subtracting a value, which is calculated by multiplying the pixel value change at the local peak value point by a predetermined ratio, from the magnitude of the pixel value change at the local peak value point.

15. A non-transitory computer readable medium including a program operating a computer to execute a method, the method comprising:

generating an edge image representing a magnitude of pixel value change per pixel in a predetermined direction in a region including an eye, based upon an image of the region including the eye;

searching a local peak value point, where the magnitude of pixel value change reaches a local peak value in the predetermined direction, in the edge image generated by the generating means; and detecting at least one of a first boundary point indicating a boundary between an upper eyelid and an eyeball and a second boundary point indicating a boundary between a lower eyelid and the eyeball, based upon a point which is shifted from the local peak value point searched by the local peak value point searching means in a direction towards the eyeball and which is closest to the local peak value point so that the magnitude of the pixel value change becomes a value obtained by subtracting a value, which is calculated by subtracting a preliminarily set value from the magnitude of the pixel value change at the local peak value point and multiplying the obtained value by a predetermined ratio, from the magnitude of the pixel value change at the local peak value point.

* * * * *